(12) United States Patent
De Yoe (10) Patent No.: US 6,430,431 B1
(45) Date of Patent: Aug. 6, 2002

(54) MRI SYSTEM FOR MEASURING VISION CAPABILITIES

(75) Inventor: Edgar A. De Yoe, Delafield, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 09/710,680

(22) Filed: Nov. 10, 2000

Related U.S. Application Data (60) Provisional application No. 60/164,715, filed on Nov. 11, 1999, and provisional application No. 60/169,236, filed on Dec. 6, 1999.

(51) Int. Cl.[7] .............................................. A61B 5/055
(52) U.S. Cl. ..................... 600/410; 600/558; 351/221
(58) Field of Search ................. 600/410, 418, 600/558; 324/307, 309; 351/205, 221

(56) References Cited

U.S. PATENT DOCUMENTS

| | | |
|---|---|---|
| 5,339,813 A | 8/1994 | DeYoe et al. |
| 5,603,322 A | 2/1997 | Jesmanowicz et al. |
| 5,662,112 A * | 9/1997 | Heid ........................... 600/410 |
| 6,009,208 A * | 12/1999 | Mitra et al. .................. 382/128 |
| 6,073,041 A * | 6/2000 | Hu et al. ..................... 600/410 |
| 2001/0031917 A1 * | 10/2001 | Rosenfeld |

OTHER PUBLICATIONS

Society For Neuroscience Abstracts, vol. 23, Part 2, 27th Annual Meeting, Oct. 25–30, 1997.
Mapping Straite and Extrastriate Visual Areas in Human Cerebral Cortex, Proc. Natl. Acad. Sci., vol. 93, No. 4–6, pp. 2382–2386 Mar. 1996, DeYoe, et al.
Functional Magnetic Resonance Imaging (fMRI) of the Human Brain, JNMEDT vol. 54, No. 2, Oct. 1994, pp. 171–187, DeYoe, et al.

* cited by examiner

*Primary Examiner*—Ruth S. Smith
(74) *Attorney, Agent, or Firm*—Quarles & Brady, LLP (57) ABSTRACT

Functional NMR data is acquired from a subject using an EPI pulse sequence while a prescribed pattern of light is displayed that stimulates locations throughout the subject's field of view. Brain activity responsive to the light stimulation is measured and a functional field map is produced which indicates all the locations in the subject's field of view which produce brain activity in the visual cortex.

13 Claims, 5 Drawing Sheets

MRI SYSTEM FOR MEASURING VISION CAPABILITIES

RELATED PATENT APPLICATIONS

This application claims benefit of Provisional Application Ser. No. 60/164,715, filed on Nov. 11, 1999 and Provisional Application Ser. No. 60/169,236, filed on Dec. 6, 1999.

BACKGROUND OF THE INVENTION

The field of the invention is the measurement of vision capabilities of a subject using functional magnetic resonance imaging (fMRI) techniques.

Functional magnetic resonance imaging (fMRI) technology provides a new approach to study neuronal activity. Conventional fMRI detects changes in cerebral blood volume, flow, and oxygenation that locally occur in association with increased neuronal activity induced by functional paradigms. As described in U.S. Pat. No. 5,603,322, an MRI system is used to acquire signals from the brain over a period of time. As the brain performs a task, these signals are modulated synchronously with task performance to reveal which regions of the brain are involved in performing the task. Much research has been done to find tasks which can be performed by patients, and which reveal in an fMRI image acquired at the same time, regions in the brain that function differently.

Functional magnetic resonance imaging has been used to create cortical maps of the retinotopic organization of human visual cortex. As described by DeYoe et al in "Functional Magnetic Resonance Imaging (fMRI) Of The Human Brain", *Journal of Neuroscience Methods*, 54 (1994) 171–187, an fMRI scan sequence is performed while providing a visual stimulation to the subject. An optical system is employed to provide a visual stimulus that changes in a prescribed manner during the fMRI scan sequence. Different regions of the retina were stimulated and the regions in the visual cortex which were responsive as measured by fMRI images were mapped. While the relationship between retinal stimulation and visual cortex response was thus established and is of academic value, the set of fMRI images produced by such scans are of limited clinical value.

SUMMARY OF THE INVENTION

The present invention is a method and apparatus for diagnosing brain activation information produced by an fMRI scan. More particularly, an fMRI scan is performed in which the subject is visually stimulated in accordance with a prescribed vision test and a time course image data set is acquired, and a functional field map indicative of the subject's vision capability over the subjects's field of view is produced. In one embodiment of the invention perceptual vision deficits are predicted from the functional field map as a result of damage to the brain.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
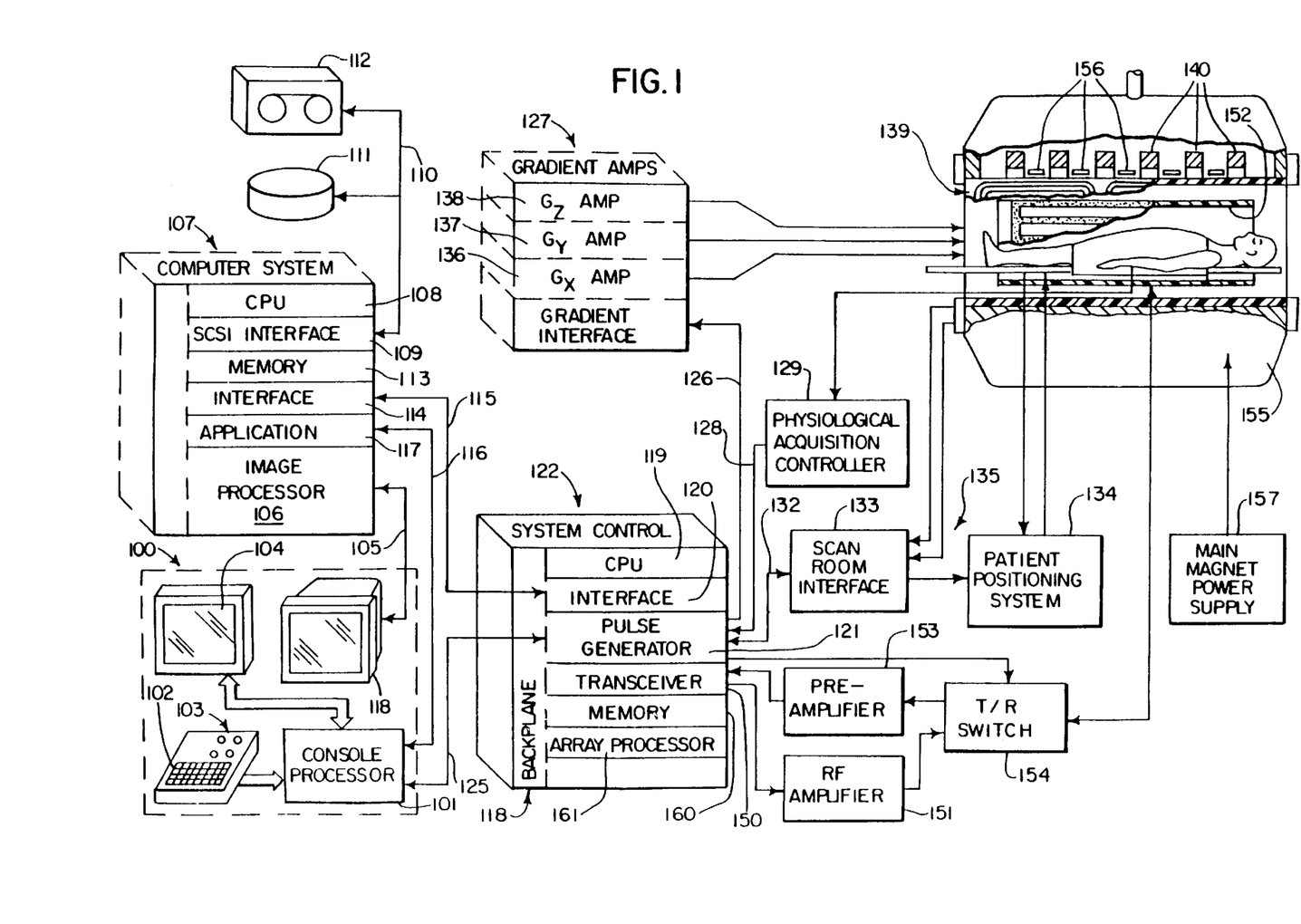
FIG. 1 is a block diagram of an NMR system which employs the present invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields In the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_O$, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_O + G_x x + G_y y G_z z$. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. As shown in FIG. 11, these local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994 and entitled "NMR Local Coil For Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is necessary in order to detect the small variations in NMR signal produced by brain functions.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter.

Figure 2:
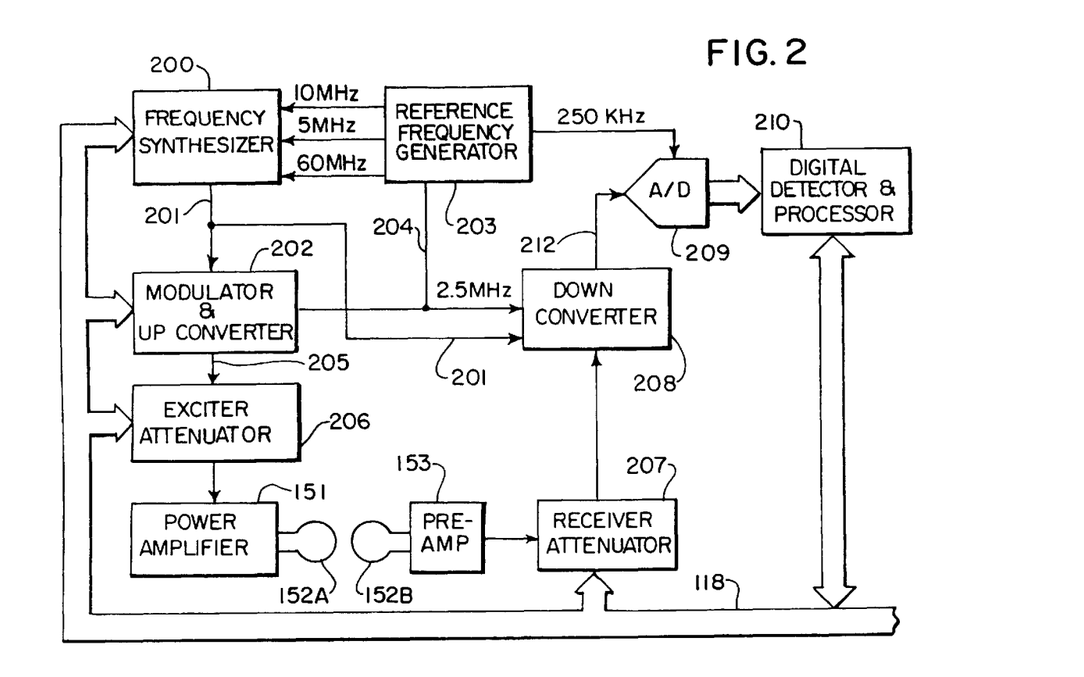
FIG. 2 is an electrical block diagram of the transceiver which forms part of the NMR system of FIG. 1.

Referring particularly to FIGS. 1 and 2, the transceiver 150 includes components which produce the RF excitation field $B_1$ through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the NMR signal produced by the subject is picked up by the receiver coil 152B and applied through the preamplifier 153 to the input of a receiver attenuator 207. In the preferred embodiment a local receive coil is used. It forms part of the coil assembly described in the above-cited U.S. Pat. No. 5,372,137. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Figure 3:
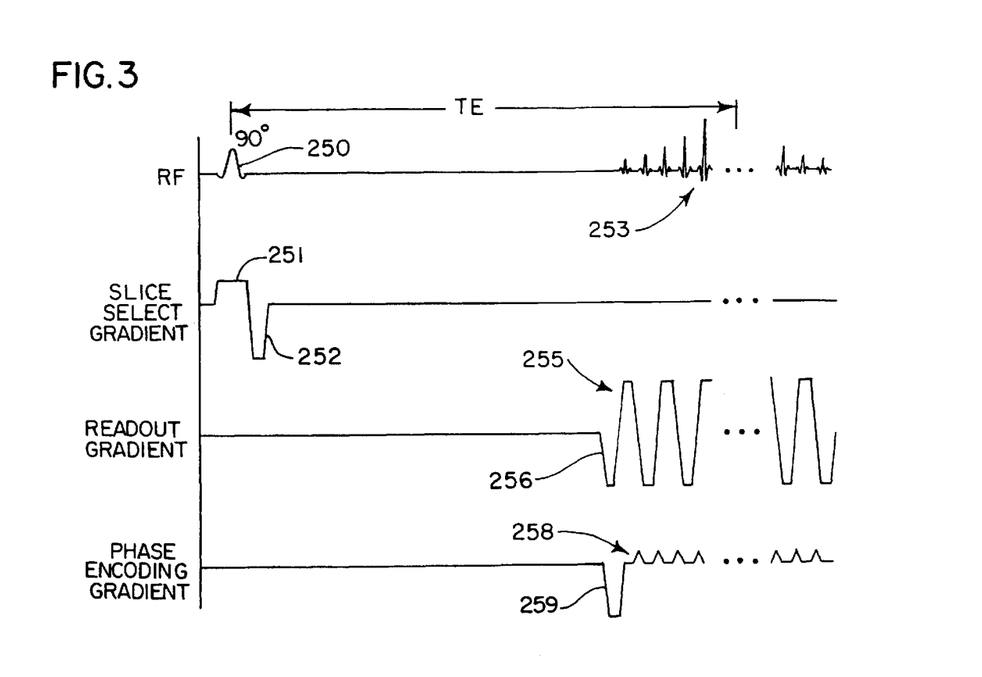
FIG. 3 is a graphic representation of the EPI pulse sequence used to practice the present invention on the NMR system of FIG. 1.

The EPI pulse sequence employed in the preferred embodiment of the invention is illustrated in FIG. 3. A 90° RF excitation pulse 250 is applied in the presence of a $G_z$ slice select gradient pulse 251 to produce transverse magnetization in a slice through the brain ranging from 4 to 8 mm thick. The excited spins are rephased by a negative lobe 252 on the slice select gradient $G_z$ and then a time interval elapses before the readout sequence begins. A total of 64 separate NMR echo signals, indicated generally at 253, are acquired during the EPI pulse sequence. Each NMR echo signal 253 is a different view which is separately phase encoded to scan $k_y$-space from $k_y=-32$ to $k_y=+32$ in monotonic order. The readout sequence is positioned such that the view acquired at $k_y=0$ occurs at the desired echo time (TE). In the preferred embodiment an EPI pulse sequence with TE=40 ms and TR=2 sec. is used. From 10 to 12 slices having an in-plane resolution of 3.75 mm, a field of view of 24 cm and a slice thickness of 8 mm are acquired.

The NMR echo signals 253 are gradient recalled echo's produced by the application of an oscillating $G_x$ readout gradient field 255. The readout sequence is started with a negative readout gradient lobe 256 and the echo signals 253 are produced as the readout gradient oscillates between positive and negative values. A total of 64 samples are taken of each NMR echo signal 253 during each 512 microsecond readout gradient pulse 255. The successive 64 NMR echo signals 253 are separately phase encoded by a series of $G_y$ phase encoding gradient pulses 258. The first pulse is a negative lobe 259 that occurs before the echo signals are acquired to encode the first view at $k_y=-32$. Subsequent phase encoding pulses 258 occur as the readout gradient pulses 255 switch polarity, and they step the phase encoding monotonically upward through $k_y$ space.

At the completion of the EPI pulse sequence, therefore, 64 separate frequency encoded samples of 64 separately phase encoded NMR echo signals 253 have been acquired. This 64×64 element array of complex numbers is Fourier transformed along both of its dimensions ($k_y$ and $k_x$) to produce a 64×64 element array of image data that indicates the NMR signal magnitude along each of its two dimensions (y and x). The 10 to 12 slices are positioned such that NMR data is acquired from the entire visual cortex region of the subject's brain.

In order to suppress the signal from cerebral spinal fluid, the EPI pulse sequence may be preceded by an inversion recovery preparation pulse sequence. As is well known in the art, inversion recovery pulse sequences include a 180° rf excitation pulse that inverts the longitudinal spin magnetization, followed by a recovery period TI in which the longitudinal magnetization of the desired spin species recovers, but that of undesired spin species does not. In the preferred embodiment TI is set to 750 milliseconds to suppress the longitudinal magnetization of cerebral spinal fluid spins prior to performing each EPI pulse sequence.

As will be explained in more detail below, the EPI pulse sequence is typically repeated 100 times to acquire time course NMR data for 100 images. The acquired NMR data is processed in the conventional manner to produce an NMR image data set for 100 images. As explained above, a two dimensional Fourier transformation is performed by the array processor 161 (FIG. 1) and the resulting NMR image data set is stored in the disk 111 for further processing by the image processor 106 according to the present invention.

Figure 4:
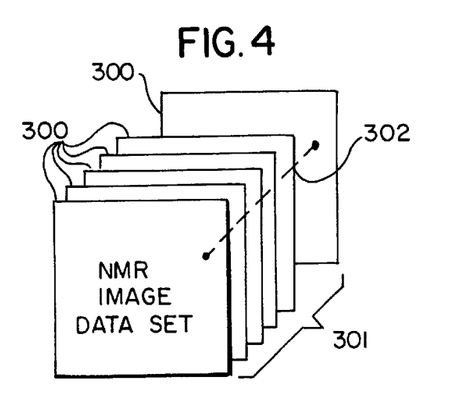
FIG. 4 is a pictorial representation of the NMR image data acquired with the pulse sequence of FIG. 3.

Referring to FIG. 4, this NMR image data set is organized as a set of 64×64 element 2D arrays 300 in which each element stores the magnitude of the NMR signal from one voxel in the scanned slice. Each array 300 can be used to directly produce a 256×256 pixel anatomical image of the brain slice for output to the video display 118. While each array 300 is a "snap shot" of the brain slice at a particular time during the time course study, the NMR image data set may also be viewed as a single 64×64×100 3D array 301 in which the third dimension is time.

Figure 5:
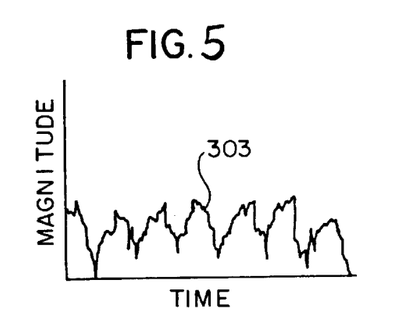
FIG. 5 is a graphic representation of a time domain voxel vector which forms part of the data set of FIG. 4.

The time course NMR image data for one voxel in the array 301 is referred to herein as a time course voxel vector. One such 100 element vector is illustrated in FIG. 4 by the dashed line 302. Each time course voxel vector 302 indicates the magnitude of the NMR signal at a voxel in the image slice over the time course study. A time domain voxel graph 303 of these magnitudes shown in FIG. 5 reveals very clearly variations in the activity of the brain in the region of the voxel.

Figures 6, 7:
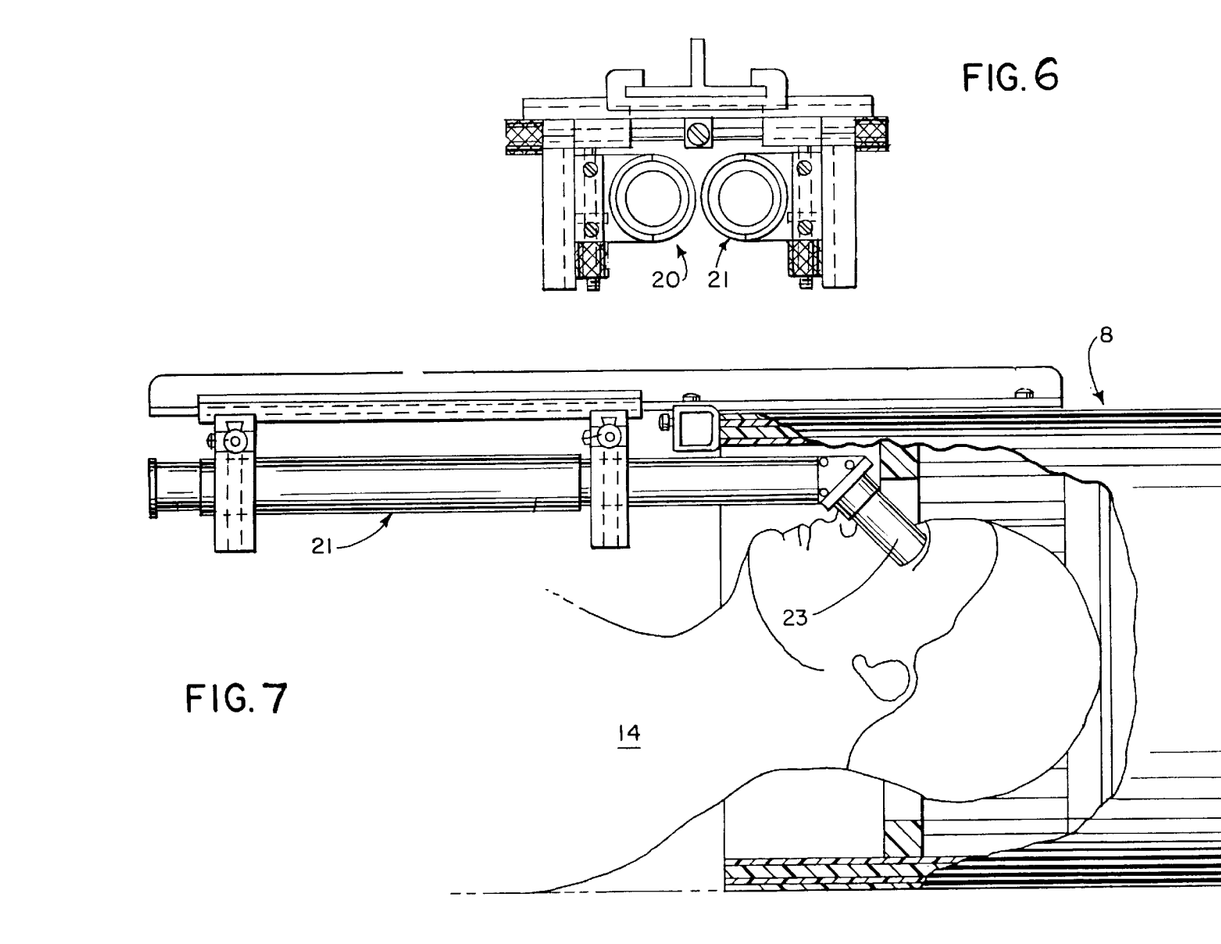
FIG. 6 is an end view of a scope used to provide visual stimulation to the subject.
FIG. 7 is a side elevation view of the scope in FIG. 6.

To practice the present invention it is necessary to provide visual stimulation to the subject during the performance of the fMRI scan. This is achieved using the patient video system described in U.S. Pat. No. 5,339,813 which is incorporated herein by reference. Referring particularly to FIGS. 6 and 7, this patient video system includes a pair of scopes 20 and 21 which are mounted to the local coil assembly 8 and positioned with their eyepieces 23 against the eyes of the patient 14. The scopes 20 and 21 are aimed along the bore axis 13 at a target area located remotely from the magnet assembly. The scopes 20 and 21 pass between the patient's face and the closely surrounding head coil 8 and they extend a substantial distance.

A display system is positioned in the target area of the scopes 20 and 21. This location is at least sixteen feet from the magnet assembly so that conventional electronic and optical technologies can be employed without damage or image distortion from the high magnetic fields. A model XG-2000 u LCD video projector commercially available from Sharp Corporation, Osaka, Japan has been modified for this purpose. The display system produces a 2"×2" color image at a front opening in response to a conventional RGB video signal received from a computer. The computer receives the image data from disc storage or it may be computed in real-time, and in brain function experiments, a sequence of images may be played out in a repetitive pattern. The two inch square image produced by the display is magnified by the scopes 20 and 21 to form an image which fills the patient's field of view.

Figure 8:
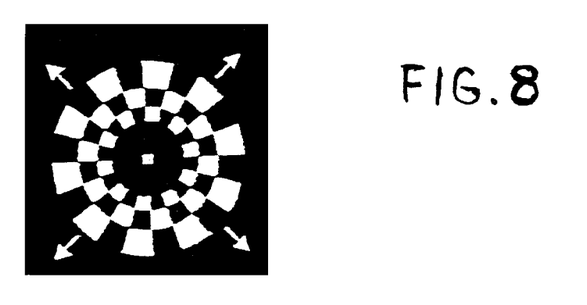
FIG. 8 is a pictorial representation of a pattern displayed to the subject through the scope of FIGS. 6 and 7.

To map angular positions within the visual field, subjects viewed a flickering, black and while checkered hemifield (mean luminance approx. 20 cd/m$^2$) that rotates slowly (one revolution every 40 seconds) about a central fixation point during the fMRI scan. To map visual field eccentricity (distance from the center of gaze), subjects viewed an expanding checkered annulus as illustrated in FIG. 8. The rate of expansion of the annulus is not linear. Rather, its distance from the center as well as the difference between the inner and outer radii of the annulus (its width) and the check size are scaled in proportion to the mean radius. Thus, the annulus moves faster, becomes wider and contains larger checks as it expands into the periphery. This provides a roughly linear expansion of the evoked neural activity in the brain because of the well known property of "cortical magnification of the fovea". By this principle, distances near the observer's center of gaze are expanded within the neural maps of visual space in the brain. The described stimulation scheme allows for a more detailed and regular sampling of the cortical map than would otherwise be possible. In this manner, neurons responding to stimulation at different locations in the visual field were activated at different times during the stimulus sequence. Corresponding differences in the temporal phase of the fMRI response thus identified the retinotopic location yielding a maximal response for each active site in the brain. To enhance activation and help maintain attention and arousal, subjects were required to detect a small target flashed at random positions superimposed on the checkered hemifield or annulus, while maintaining fixation.

Cortical sites of significant activation in the subject's brain were identified by cross-correlating the response waveform for each time course voxel vector 302 with a reference voxel vector in the form of a sine function that closely approximates the ideal response to the visual stimulus smoothed and delayed by the cortical hemodynamics. Under the null hypothesis (no signal present), the cross-correlation coefficient follows the incomplete beta distribution, thereby permitting calculation of the statistical significance, p, based on 96 degrees of freedom in the MR time series (100 minus 4 fit coefficients for the phase and amplitude of the reference waveform). In the present experiments, voxels were considered active if they each passed a threshold of $p<=6.2\times10^{-8}$, (corresponding to $r>=0.54$ for 96 degrees of freedom). Using a Bonferroni correction for multiple comparisons this is equivalent to $p<=0.003$ for the entire brain volume.

In order to construct beam activation maps, all voxels exceeding the criterion may be displayed with the color of each voxel representing the amplitude of the best-fit reference waveform. The resultant functional images can then be combined with anatomical images and assembled into a combined 3-dimensional, volumetric data set that can be displayed if desired. In this manner, the visual stimulation of each location in the subjects's field of view may be associated with specific locations/voxels in the visual cortex that are activated. In order to enhance further display and analysis of the imaging data, high-resolution spoiled GRASS structural images at 1.1 mm thickness (TE=6 ms, TR=48 ms, FOV=24 cm, Resolution=256×192, FA=40, NEX=1) were obtained in the axial plane for each subject and then used to construct brain models and identify anatomically abnormal cortex.

Figure 9:
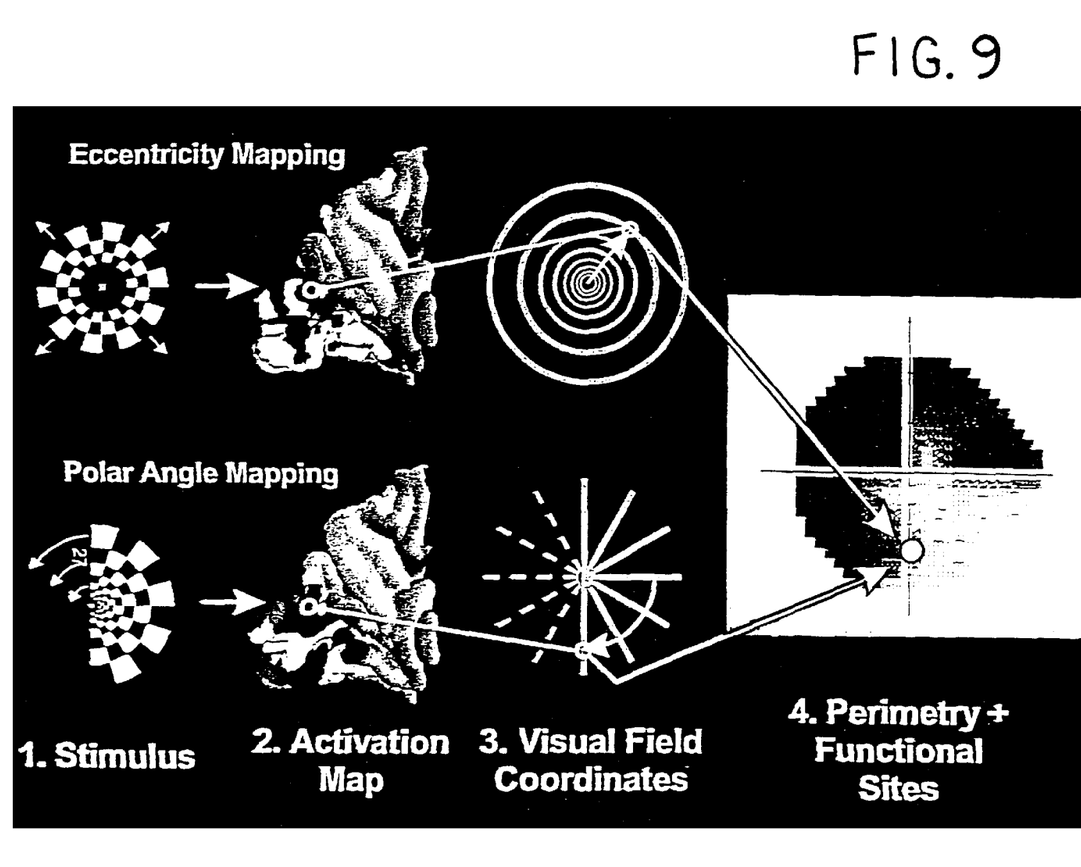
FIG. 9 is a pictorial representation of the process employed to produce a functional field map according to the preferred embodiment of the invention.

The fMRI mapping data are converted into a functional field map that permits direct visualization of the pattern of blindness within the subject's field of view. This process is illustrated in FIG. 9. The retinotopic mapping measurements described above identified optimal visual field eccentricity (expanding ring) and polar angle (rotating hemifield) for activating individual voxels in the subject's visual cortex. For each responsive voxel, the annulus and hemifield mapping measurements yield the polar coordinates of the visual field position that, when stimulated in the prescribed pattern, induce the maximum response. To create the functional field map, a symbol is placed at the corresponding coordinates on a diagram of the subject's visual field. The color of the symbol is chosen from a pseudocolor scale representing the amplitude of the fMRI response for that voxel. The size of the symbol is scaled according to the estimated 90% confidence zone for the true location of the data point. This procedure is repeated for all responsive voxels or for selected subsets of voxels as desired. Note, that in a fully sighted individual there will be symbols on the functional field map for all locations in the field of view. For patients having localized areas of blindness, there will be few, or no, voxels at the corresponding visual field locations. Also note that the functional field map is calculated directly from the fMRI signals without reference to their physical location in the brain.

Calibration of the coordinates for the functional field map requires some care. The sluggishness of the cortical hemodynamic mechanisms introduces a delay of 6–8 seconds between the onset of visual stimulation and the peak of the evoked fMRI response. This translates into a fixed offset in the measured eccentricity and polar angle coordinates for each voxel. Although, in theory, this offset could be different for each voxel, empirical measurement of the variability in the hemodynamic delay indicates that it is constant to within ±3.6 seconds across voxels and across visual areas. To estimate accurately this offset for each subject, the visual field mapping using both contracting and expanding annuli, and clockwise and counter-clockwise rotating hemifields is repeated. For the hemifields, the rotation cycle started at the 12:00 position on the superior vertical meridian. Only voxels representing the vertical meridian could have equivalent delays for both clockwise and counter-clockwise rotation. Consequently, the combined set of responsive voxels for the two hemifield experiments was searched for voxels having matched phase delays for each direction of rotation. The phase delays for the 10 best matched voxels averaged and the result was used to calculate the offset between the true phase delay of the stimulus at the 6:00 position and the actual measured phase delay of the best matched voxels. As an independent check, the same computation was performed for the two annulus experiments. Since both estimates of the offset agreed well, the two were averaged to provide the best estimate from the combined data set.

The results of the Functional Field Mapping analysis showed that there was a close relationship between the retinotopic organization of medial visual cortex and the pattern of blindness caused by cortical pathology. The analysis was sufficiently precise to account for details of the behavioral data such as macular sparing. In fact, the functional field map provides a more accurate prediction of the pattern of visual field defects than can be obtained from consideration of the anatomy of the lesions alone.

An advantage of the functional field map is that the pattern of visual field defects can be estimated directly from the fMRI data without the need to produce an intervening anatomical map of brain activation. Although such brain maps may be created to illustrate the distribution of activity, they are not a requisite step in the creation of the function field map. Consequently, potential errors associated with the creation of anatomical brain maps are avoided.

The functional field mapping suggests that the retinotopic organization within eloquent cortex can be somewhat irregular yet still be compatible with the detailed pattern of sighted and blind regions. Hypothetically, the voxels representing the points in the functional field map can be re-arranged or even randomly scrambled within the cortex without affecting the map. Moreover, distortions of the cortical retinotopic maps due to distortions of the anatomy or re-organization will not affect the functional field map unless voxels representing a particular position in the visual field are either added or deleted.

By using fMRI to estimate directly the visual field locus represented by each active voxel, functional field mapping circumvents the vagaries of individual anatomy. In principle, it permits a more accurate determination of the relationship between brain activity and visual sensation. To the extent that a lesion disrupts the brain activity, it directly affects the functional field map, and this will be true regardless of whether the lesion involves gray matter or the underlying white matter. In turn, this provides an opportunity to test the relationship between brain function and sensory experience in a specific, and quantitative fashion that has not been possible.

A final advantage of the functional field mapping method is that it can be easily adapted to the display of other visual functions. Once voxels in the brain have been indexed to a location in the patient's field of view, then any other vision assessment procedure that produces activation in those same voxels can be displayed in functional field map format.

As described above, each symbol on the functional field map is assigned a color representing the intensity of the brain activation evoked by a stimulus at the corresponding position in the patient's field of view. However, the color scheme can be replaced by one that represents the results of other vision capability measurements. These measurements may include, for example, the intensity of the subject's visual attention at that visual field location or by colors representing an fMRI measure of visual contrast sensitivity. In sum, this technique provides a general purpose method for displaying any brain-derived measurement of vision capacity that is distributed across the patient's field of view.

What is claimed is:

1. A method for measuring vision capability in a subject, the steps comprising:
   a) acquiring with a magnetic resonance imaging system a series of NMR image data arrays over a period of time to form a time course NMR image data set comprised of time domain voxel vectors which indicate the NMR signals from respective regions of the subject's brain during said period of time;
   b) visually stimulating the subject during said period of time in a prescribed pattern at each of a plurality of locations in the subject's field of view;
   c) producing reference time domain voxel vectors indicating the prescribed pattern at each of the plurality of locations;
   d) calculating the correlation between reference time domain voxel vectors and the time domain voxel vectors to measure brain activity in response to the prescribed pattern of visual stimulation; and
   e) producing a functional field map which indicates the locations in the subject's field of view which produce brain activity as measured by the calculated correlations.

2. The method as recited in claim 1 in which the visual stimulation is produced by displaying a light at a location in the subject's field of view and turning the light on and off in a prescribed pattern.

3. The method as recited in claim 2 in which the prescribed pattern is to turn the light on and off over a series of equal time intervals at a prescribed frequency.

4. The method as recited in claim 3 in which the reference time domain voxel vector is substantially sinusoidal in amplitude and has the prescribed frequency.

5. The method as recited in claim 2 in which the visual stimulation includes repeating the prescribed pattern with the light positioned at different locations in the subject's field of view.

6. The method as recited in claim 5 in which the light is moved to successive radial distances from the center of the subject's field of view.

7. The method as recited in claim 6 in which the light is also moved to successive polar angle locations around the center of the subject's field of view.

8. The method as recited in claim 7 in which step e) is performed by combining the brain activity indication responsive to the light moving radially to positions in the subject's field of view with the brain activity indication responsive to the light moving azimuthally to positions in the subject's field of view.

9. The method as recited in claim 5 in which the light is moved to successive polar angle locations around the center of the subject's field of view.

10. The method as recited in claim 1 in which the NMR signals are acquired with a gradient-recalled pulse sequence.

11. The method as recited in claim 10 in which the pulse sequence is an echo-planar imaging pulse sequence.

12. The method as recited in claim 1 which includes:
   f) relating locations of brain activity to locations in the subject's field of view;
   g) repeating steps b), c) and d)using a different prescribed visual stimulation pattern to measure a different visual capability of the subject; and
   e) displaying on the functional field map indications of the subjects' different visual capability.

13. The method as recited in claim 12 in which the different visual capability is visual attention.

* * * * *

UNITED STATES PATENT AND TRADEMARK OFFICE
CERTIFICATE OF CORRECTION

PATENT NO.    : 6,430,431 B1
DATED         : August 6, 2002
INVENTOR(S)   : De Yoe It is certified that error appears in the above-identified patent and that said Letters Patent is hereby corrected as shown below:

Column 1,
Line 8, insert the following:
-- STATEMENT REGARDING FEDERALLY SPONSORED RESEARCH OR DEVELOPMENT The U.S. government has a paid-up license in this invention and the right in limited circumstances to require the patent owner to license others on reasonable terms as provided for by the terms of contract No. RO1EY10244 awarded by the National Eye Institute of the National Institutes of Health. --

Signed and Sealed this

Seventh Day of October, 2003

JAMES E. ROGAN
*Director of the United States Patent and Trademark Office*